(12) United States Patent
Kremminger et al.

(10) Patent No.: US 9,169,239 B2
(45) Date of Patent: Oct. 27, 2015

(54) PROCESS FOR PREPARING CEFTAROLINE FOSAMIL

(75) Inventors: Peter Kremminger, Kufstein (AT); Hubert Sturm, Innsbruck (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 14/343,723

(22) PCT Filed: Sep. 7, 2012

(86) PCT No.: PCT/EP2012/067550
§ 371 (c)(1),
(2), (4) Date: Jun. 12, 2014

(87) PCT Pub. No.: WO2013/034718
PCT Pub. Date: Mar. 14, 2013

(65) Prior Publication Data
US 2015/0073138 A1    Mar. 12, 2015

(30) Foreign Application Priority Data
Sep. 9, 2011    (EP) .................................... 11180728

(51) Int. Cl.
*C07D 417/04* (2006.01)
*C07D 501/59* (2006.01)
*C07D 501/08* (2006.01)

(52) U.S. Cl.
CPC ............ *C07D 417/04* (2013.01); *C07D 501/08* (2013.01); *C07D 501/59* (2013.01)

(58) Field of Classification Search
CPC .................................................... C07D 417/04
USPC ...................................................... 546/270.4
See application file for complete search history.

(56) References Cited

FOREIGN PATENT DOCUMENTS

EP    1 310 502 A1    5/2003

OTHER PUBLICATIONS

T. Ishikawa et al., TAK-599, a novel N-phosphono Type Prodrug of Anti-MRSA Cephalosporin T-91825: Synthesis, Physicochemical and Pharmacological Properties, Bioorganic & Medicinal Chemistry, vol. 11, pp. 2427-2437 (2003).

*Primary Examiner* — Kahsay Habte
(74) *Attorney, Agent, or Firm* — IPLM Group, P.A.

(57) ABSTRACT

The present invention relates to a novel process for preparing ceftaroline fosamil as well as to intermediates of Formulae (1), (3) or (4) of this process.

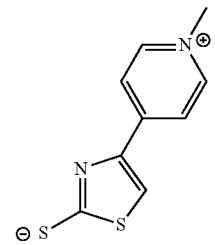

(1)

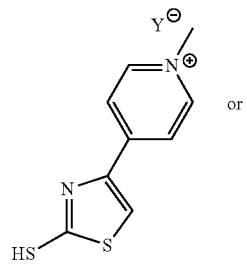

(3)

or

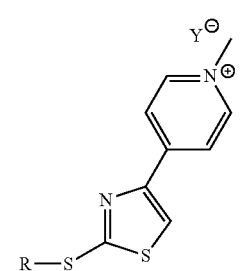

(4)

7 Claims, No Drawings

PROCESS FOR PREPARING CEFTAROLINE FOSAMIL

CROSS REFERENCE TO RELATED APPLICATION

This application is a national stage filing under 35 U.S.C. §371 of International Application No. PCT/EP2012/067550 filed Sep. 7, 2012, which claims priority under 35 U.S.C. §119(b) and 37 CFR 1.55(a) to European Application No. 11180728.5 filed Sep. 9, 2011, the disclosures of both of which are incorporated herein by reference.

FIELD OF THE INVENTION

The present invention relates to a novel process for preparing ceftaroline fosamil as well as to intermediates of this process.

BACKGROUND OF THE INVENTION

Ceftaroline fosamil ((6R,7R)-7-[(2Z)-2-ethoxyimino-2-[5-(phosphonoamino)-1,2,4-thiadiazol-3-yl]acetyl]amino]-3-[4-(1-methylpyridin-1-ium-4-yl)-1,3-thiazol-2-yl]sulfanyl]-8-oxo-5-thia-1-azabicyclo[4.2.0]oct-2-ene-2-carboxylate; Teflaro) is a cephalosporin antibiotic which is active against methicillin-resistant *Staphylococcus aureus* and Gram-positive bacteria. It has the general formula

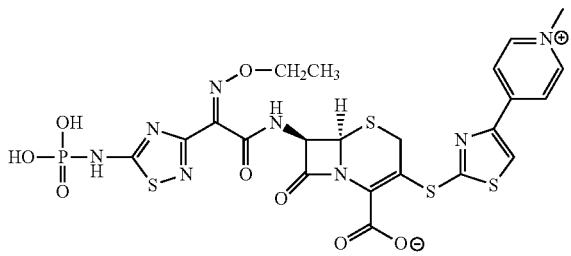

whereby the compound is generally provided in the form of its acetic acid solvate.

EP-A-1 310 502 discloses a process for preparing ceftaroline fosamil in which a side chain is first introduced into a compound having the formula (III) (Ph=phenyl, BH=benzhydryl). Because a base is generally required for this reaction step, undesired by-products can be formed. The nitrogen atom of the compound having the formula (V) is then quaternized in a subsequent reaction step using methyl iodide.

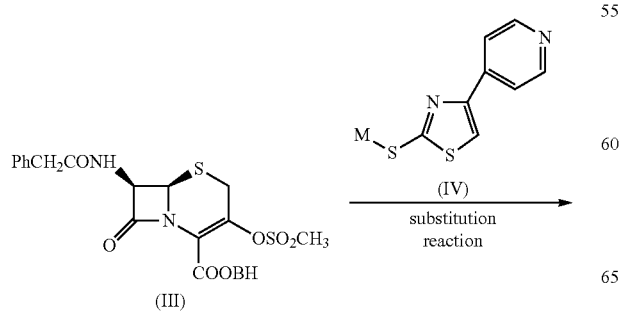

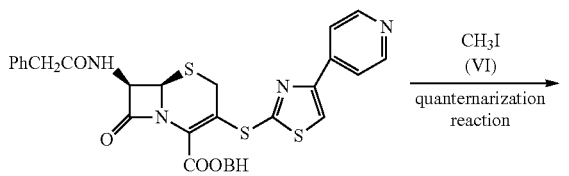

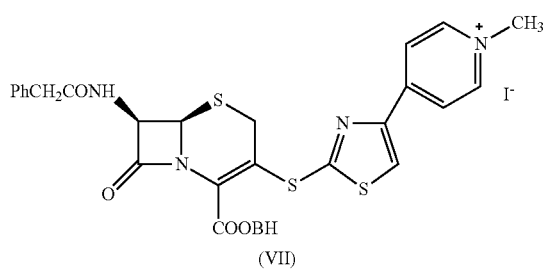

A similar reaction is also described in T. Ishikawa et al., *Bioorganic & Medicinal Chemistry*, 11 (2003) 2427-2437.

It was previously considered essential that the substitution reaction should be conducted before the methylation reaction because the selective methylation of the nitrogen atom in the presence of a thiol was considered difficult and the corresponding intermediates were unstable.

It was an object of the present invention to provide an improved process for producing ceftaroline fosamil which requires less reaction steps. It was a further object of the present invention to provide an improved process for producing ceftaroline fosamil which results in a lower formation of by-products.

SUMMARY OF THE INVENTION

The present invention relates to a compound selected from the group consisting of

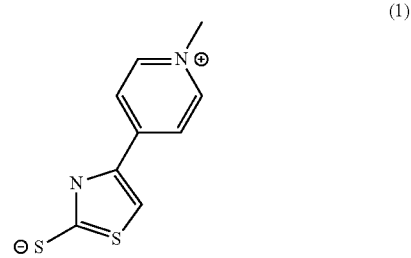

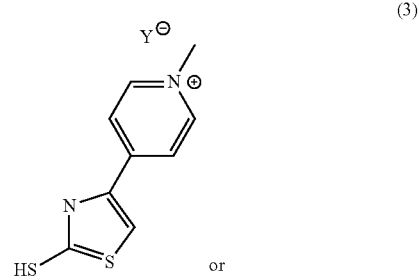

-continued (4)

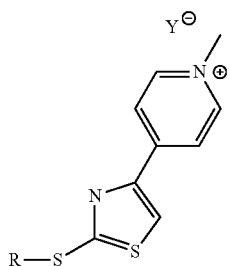

wherein

R is R¹—C(O)— (with R¹ being $C_{1-12}$ alkyl, preferably $C_{1-4}$ alkyl) or R²—O—C(O)— (with R² being $C_{1-4}$ alkyl, benzyl or phenyl, preferably $C_{1-4}$ alkyl); and $Y^\ominus$ is an anion.

A preferred embodiment of compound (4) is an acetate which is referred to as compound (2):

(2)

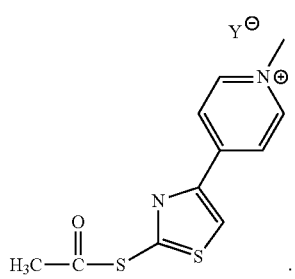

These compounds will be collectively referred to as compounds having the formula (I) or compounds of the present invention in the following.

Processes of preparing these compounds are subject-matter of the present invention.

In a further embodiment the present invention refers to the use of a compound having the formula (I) for the preparation of ceftaroline fosamil.

Another embodiment of the present invention relates to a process comprising:

(i) reacting a compound having the formula (1), (3) or (4) as defined above with an activated form of a compound having the formula (5)

(5)

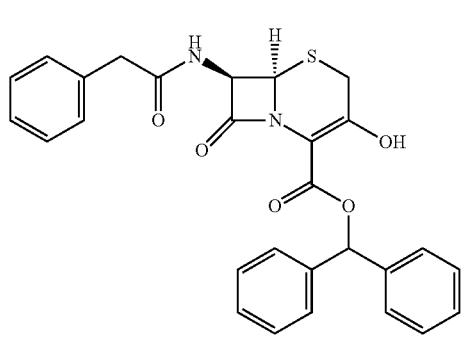

to provide a compound having the formula (6)

(6)

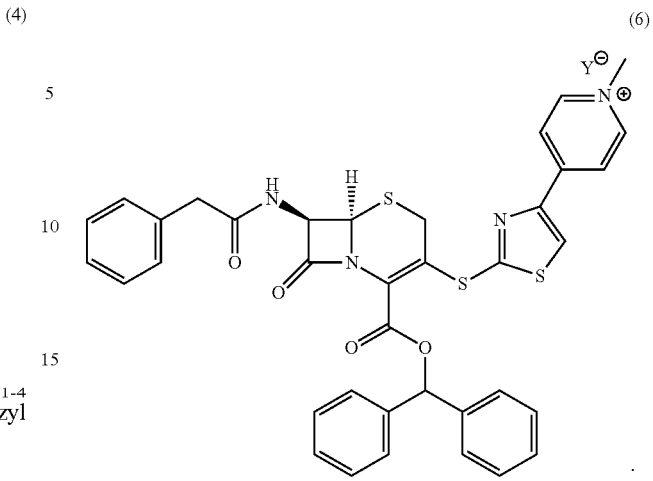

The term "activated form of a compound having the formula (5)" refers to a compound having the formula (5) in which the —OH group is activated. Examples of activated forms of the compound having the formula (5) include, but are not limited to, sulfonate esters (such as mesylate, tosylate, triflate) and phosphate esters (such as biphenyl phosphate). Sulfonate esters are preferred and mesylate is particularly preferred.

If desired, these processes can further comprise one or more of the following steps:

(ii) reacting a compound having the formula (6) to provide a compound having the formula (7) or a salt thereof (7)

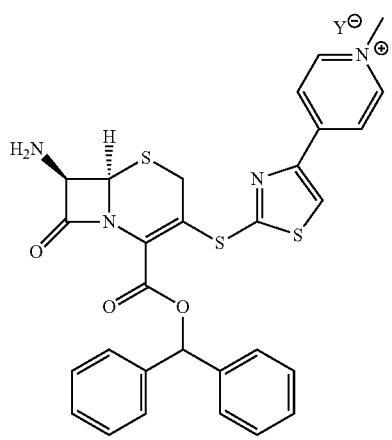

(iii) reacting a compound having the formula (7) to provide a compound having the formula (8) or a salt thereof (8)

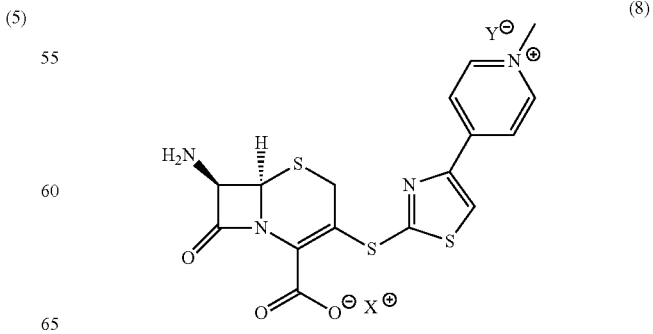

wherein $X^\oplus$ and $Y^\ominus$ are optionally present;

(iv) reacting a compound having the formula (8) with a compound having the formula (9)

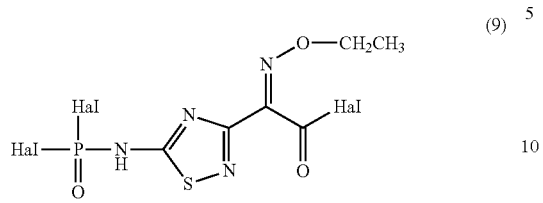

wherein Hal is a halogen;

to provide a compound having the formula (10) or a salt thereof

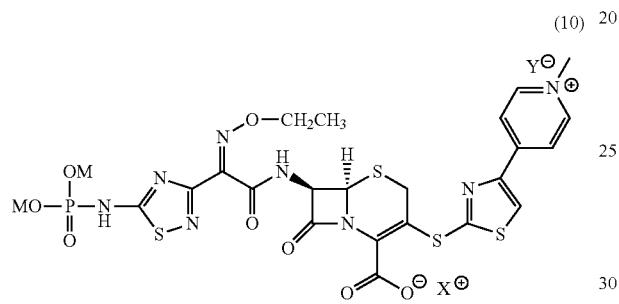

wherein M is hydrogen or a metal, and $X^{\oplus}$ and $Y^{\ominus}$ are optionally present;

(v) if the compound having the formula (10) has M=metal cation, then reacting the compound having the formula (10) to provide a compound having the formula (11)

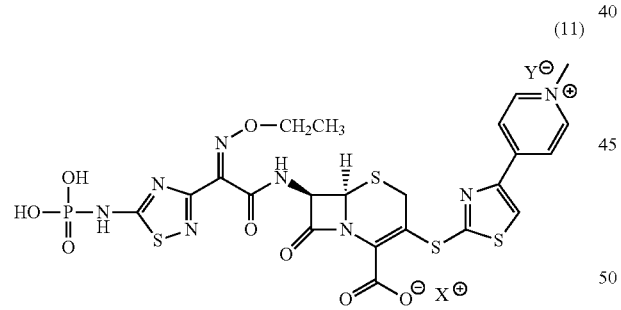

wherein $X^{\oplus}$ and $Y^{\ominus}$ are optionally present; and wherein $X^{\oplus}$ (when present) is H;

(vi) optionally transforming the compound having the formula (11) into a pharmaceutically acceptable salt, solvate or hydrate thereof.

It is understood that the counterions $X^{\oplus}$ and $Y^{\ominus}$ (when present) do not have to be the same throughout the processes described herein but can be the same or different in the individual reaction steps.

If M is a metal, the metal is not particularly limited. Illustrative examples include alkali metals and alkaline earth metals. It is understood that number of metal cations is adapted, so that a compound having neutral charge is achieved.

DETAILED DESCRIPTION OF THE INVENTION

The compounds of the present invention are selected from the group consisting of

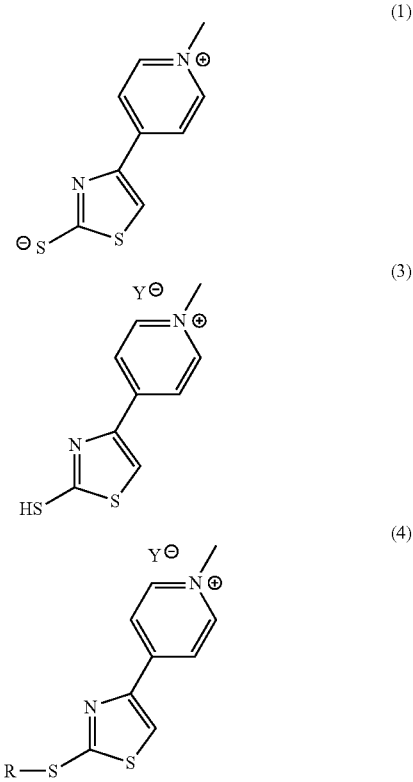

The compound having the formula (1) is a zwitterion, whereas the compounds having the formulae (3) and (4) are salts.

$X^{\oplus}$ is a cation such as an alkali metal, e.g., sodium or potassium, or an ammonium cation. Organic ammonium cations (e.g., tri($C_{1-8}$ alkyl)ammonium cations or tetra($C_{1-8}$ alkyl)guanidinium cations) and inorganic ammonium cations ($NH_4^+$) can also be employed.

$Y^{\ominus}$ is an anion such as a halogenide (e.g., chloride or bromide), trifluoroacetate, methane sulfonate, trifluoromethane sulfonate, toluene-4-sulfonate, tetrafluoroborate, acetate, hexafluorophosphate or hexafluoroantimonate.

Compounds Having the Formulae (1) and (4)

The methods for preparing compounds having the formulae (1) or (4) are not particularly restricted. One option is shown in the following scheme.

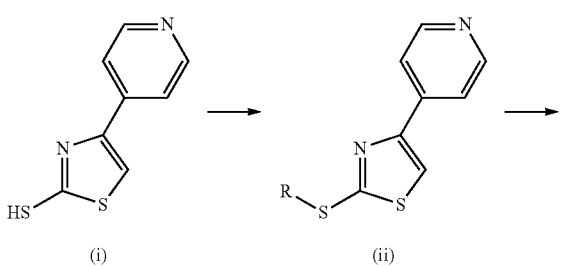

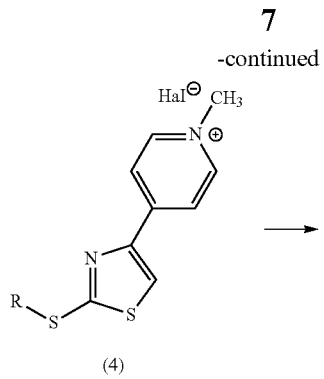

In this embodiment [4-(4-pyridyl)-1,3-thiazol-2-yl]thiol (compound having the formula (i)) is reacted to the compound having the formula (ii). This reaction can be conducted by reacting with a suitable acylating agent, such as an anhydride (such as a $C_{1-6}$ alkyl anhydride, e.g., acetic anhydride) or a halogenoformate (such as a $C_{1-6}$ alkyl halogenoformate, phenyl halogenoformate or benzyl halogenoformate, with halogen preferably being chlorine, e.g., ethyl chloroformate or benzyl chloroformate), optionally in the presence of a solvent, and optionally in the presence of a base. Examples of bases are strong bases such as those having a $pK_a$ of ≥12. These include, e.g., $C_{1-8}$ alkyl, tri($C_{1-8}$ alkyl)amines, $C_{1-8}$ alkoxides, NaH, diazabicycloundecene and tetramethylguanidine, whereby tetramethylguanidine is preferred.

The resultant compound having the formula (ii) can be reacted with a methylating agent to the compound having the formula (4). This reaction can, for example, be conducted using methyl halogenide such as methyl iodide.

The obtained compound having the formula (4) can then be reacted to the desired compound (1), [4-(N-methylpyridinium-4-yl)-1,3-thiazol-2-yl]thiolate, by removing the group —R. In one embodiment this reaction can be effected by using an aqueous base, such as ammonia, primary ($C_{1-6}$ alkyl)amine, carbonate solution or hydrogen carbonate solution, whereby hydrogen carbonate solution is preferred.

A related option is shown in the following scheme:

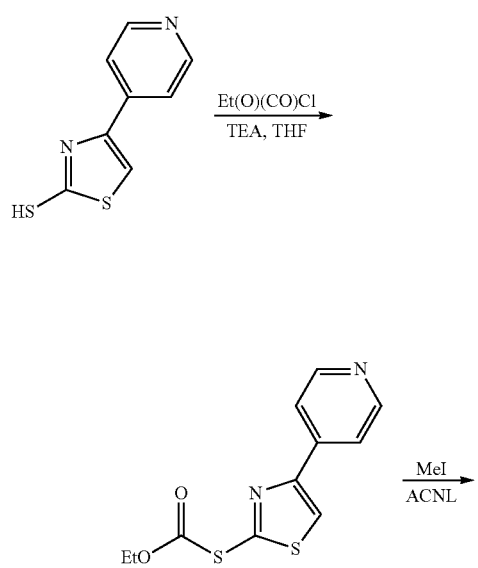

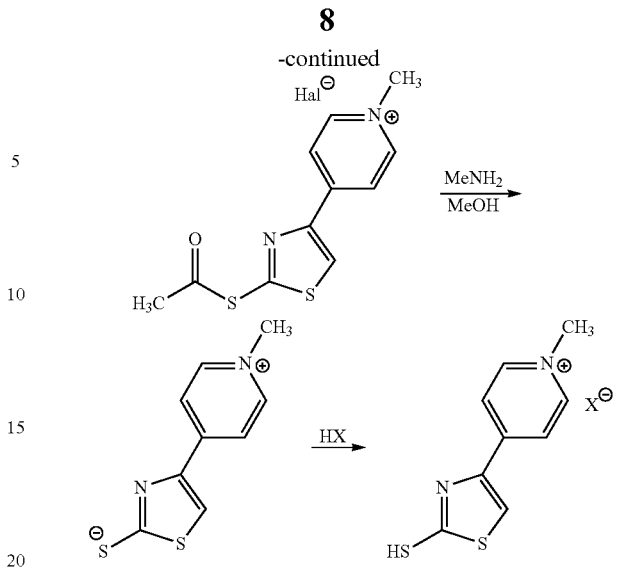

In this reaction it is also possible to use $CH_3C(O)—$ instead of $Et(O)(CO)—$.

Compounds Having the Formula (3)

The method of preparing the compounds having the formula (3) is not particularly restricted, either. According to one option, the compounds having the formula (3) can be prepared as follows:

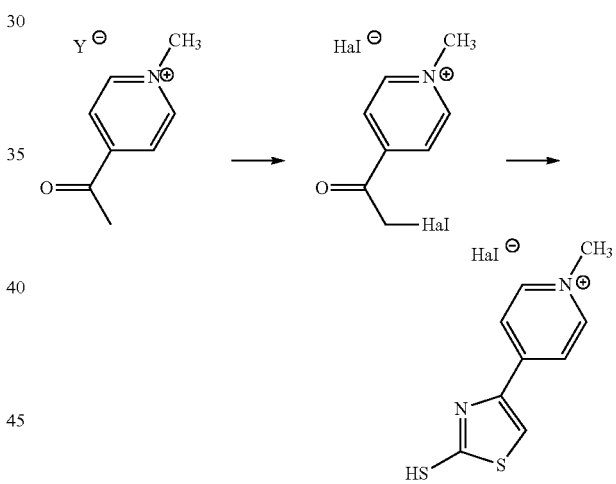

In a first step 4-acetyl-1-methylpyridinium salt (e.g., halogenide such as iodide) can be reacted to provide 4-(2-halogenoacetyl)-1-methylpydridinium halogenide, in which the halogen is preferably chloro or bromo. The reaction conditions are not particularly restricted and will depend on the specific halogen desired. The bromo compound can be, e.g., prepared using hydrogen bromide and bromine, while the chloro compound can be, for example, prepared using sulfuryl chloride.

The desired compound having the formula (3) can then be prepared by reacting the 4-(2-halogenoacetyl)-1-methylpydridinium halogenide, for example, with a dithiocarbamate such as ammonium dithiocarbamate.

It is also possible to modify this process by adding a further step in which the compound having the formula (3) is reacted with an aqueous base, such as ammonia, carbonate solution or hydrogen carbonate solution, whereby hydrogen carbonate solution is preferred. If this additional step is conducted, a compound having the formula (1) is obtained.

In an alternative embodiment, the compounds having the formula (3) can be prepared from the compounds having the formula (1).

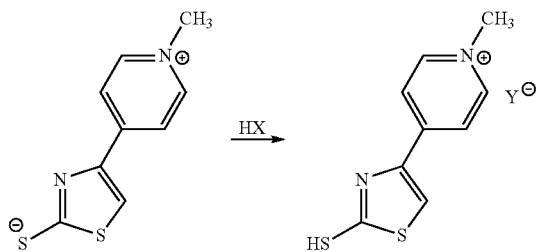

In this embodiment, [4-(4-(1-methylpyridyl)-1,3-thiazol-2-yl]thiolate is reacted with the acid HY which corresponds to the desired salt. Examples of suitable acids include acetic acid, trifluoroacetic acid, methane sulfonic acid, trifluoromethane sulfonic acid, para-toluene sulfonic acid, hydrohalogenic acids (such as hydrochloric acid), tetrafluoroboric acid, hexafluorophosphoric acid and hexafluoroantimonic acid. Halogen salts can also be provided, e.g., by reaction with silyl compounds such as trialkylsilyl halogenide (wherein the alkyl group has, for example, 1 to 4 carbon atoms, preferably 1 carbon atom and wherein the halogenide is preferably chloride).

Applications

Step (i):

The compound having the formula (1), (3) or (4) can be reacted with an activated form of the compound having the formula (5)

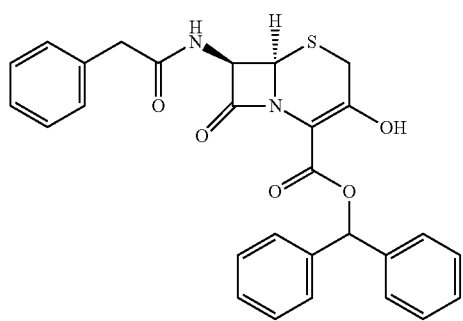

to provide a compound having the formula (6)

In a first step, the compound having the formula (5) is activated, for example, by reacting it with a corresponding activating agent. Possible activated forms are sulfonates (such as mesylate, tosylate, or triflate) or phosphates (such as biphenyl phosphate). This can be achieved by reacting the compound having the formula (5) by reacting it with an activating agent (e.g., the halogenides or anhydrides of the corresponding acids in the presence of a base such as tri($C_{1-6}$ alkyl)amine. A preferred activated form is the mesylate.

Then the compound having the formula (1), (3) or (4) is added to effect the reaction. The reaction conditions are not particularly restricted and will depend on the specific reactants chosen. The reaction will, however, be typically conducted in the presence of a base. During the reaction the pH will, for example, be in the range of about 2 to about 7, preferably from about 3 to about 5. The base can be, for example, selected from the group consisting of hydrogen carbonates, carbonates, carboxylates or organic amines (such as tri($C_{1-6}$ alkyl amines). Preferably the base is a hydrogen carbonate. This has the advantage that the reaction between the compounds having the formula (3) and (4) and the compound having the formula (12) is much faster than the previously disclosed procedure, and can be conducted under milder conditions than those previously known which results in less production of by-product.

The reaction solvent is not particularly limited and can be any suitable organic solvent. Examples of possible solvents include nitrile solvents (such as acetonitrile), ketones (such as acetone), ethers (such as tetrahydrofuran), amides (such as dimethylformamide) or dimethylsulfoxide. Preferably the solvent is a nitrile solvent.

The reaction will be usually conducted at ambient temperature (approx. 25° C.) but other reaction temperatures are also possible.

If desired, the compound having the formula (6) can be isolated and/or purified according to known procedures or can be used as such in a subsequent reaction step.

The compounds having the formula (I) are useful for the preparation of ceftaroline fosamil, whereby the process is not particularly limited.

In one preferred embodiment the process comprises the step (i) and optionally one or more steps (ii) to (vi).

Step (ii):

The compound having the formula (6) can be reacted to provide a compound having the formula (7) or a salt thereof

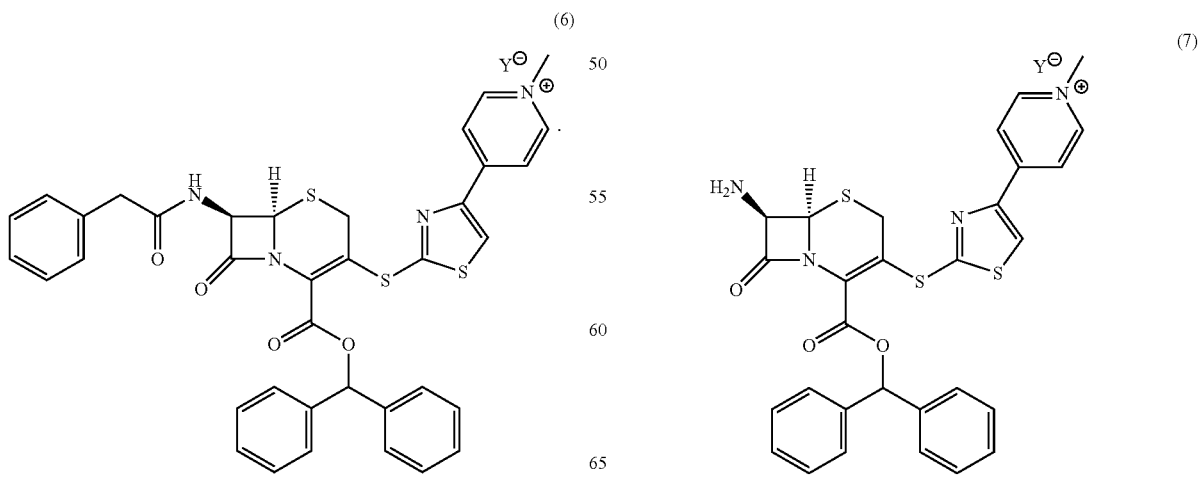

In this step, the amide bond connecting the phenylacetyl group can be cleaved by any suitable method. According to one option, the reaction can be conducted using phosphorus pentachloride and a tertiary amine.

Step (iii):

The compound having the formula (7) is subsequently reacted to provide a compound having the formula (8) or a salt thereof

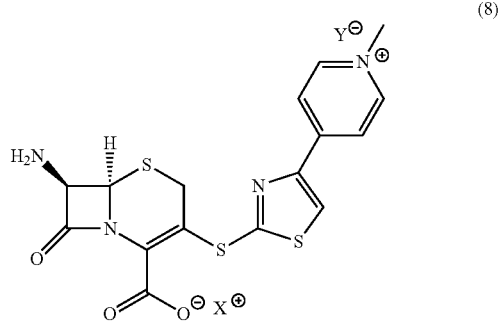

(8)

wherein $X^\oplus$ and $Y^\ominus$ are optionally present.

This reaction can be achieved by various methods. In one embodiment, an acid is used to deprotect the carboxyl group.

Step (iv):

The compound having the formula (8) is then reacted with a compound having the formula (9)

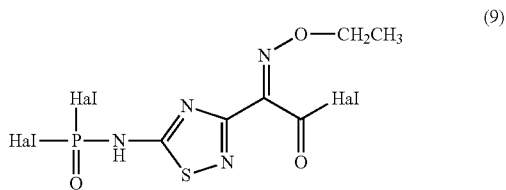

(9)

wherein Hal is a halogen (e.g., F, Cl, Br, or I; preferably Cl) to provide a compound having the formula (10) or a salt thereof

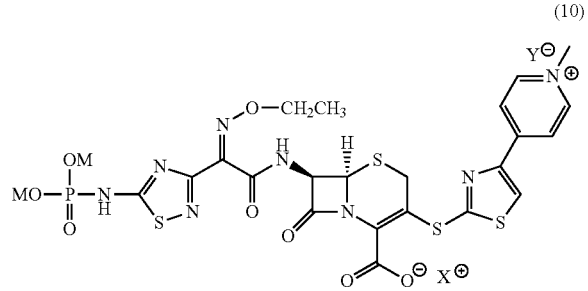

(10)

wherein M is hydrogen or a metal (e.g., an alkali metal), wherein $X^\oplus$ and $Y^\ominus$ are optionally present.

The reaction preferably takes place in the presence of an acid scavenger which captures the acid that is generated during the reaction. Examples of suitable acid scavengers include salts (e.g., sodium hydrogen carbonate, sodium carbonate, potassium carbonate, sodium acetate, potassium acetate, and sodium phosphate), tertiary amines (e.g., triethylamine, tripropylamine, tributylamine, ethyldiisopropylamine, pyridine, lutidine, N,N-dimethylaniline, N-methylpiperidine, N-methylpyrrolidine, and N-methylmorpholine), alkylene oxides (e.g., propyleneoxide, and epichlorohydrin) and mixtures thereof. Of these, a combination of sodium hydrogen carbonate, sodium carbonate, sodium acetate, triethylamine or sodium acetate with triethylamine is preferable, and particularly a combination of sodium hydrogen carbonate, sodium acetate, triethylamine or sodium acetate with triethylamine is more preferable.

Examples of possible reaction conditions for steps (ii) to (iv) can be, among others, found in EP-A-1 310 502.

Step (v):

If the compound having the formula (10) has M=metal cation, it is typically converted into the corresponding compound with M=H, i.e., a compound having the formula (11)

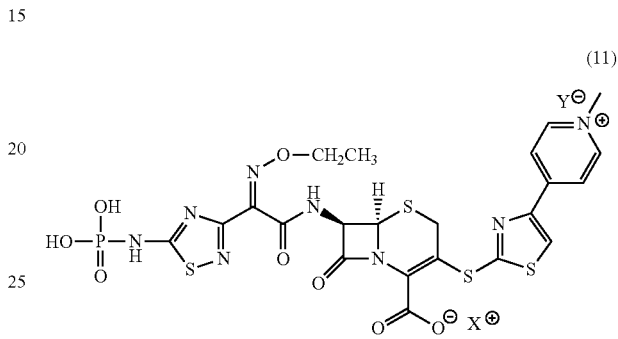

(11)

wherein $X^\oplus$ and $Y^\ominus$ are optionally present, and wherein $X^\oplus$ (when present) is H. This reaction can be conducted, e.g., by the addition of acids, such as acetic acid.

Step (vi):

If the compound having the formula (10) or (11) is not already in the form of the desired pharmaceutically acceptable salt, solvate or hydrate, it can be optionally transformed into the desired pharmaceutically acceptable salt, solvate or hydrate. The method of transforming is not particularly limited and will depend on the starting material and the desired final compound. In one embodiment, the compound having the formula (10) or (11) can be crystallized from a suitable aqueous or organic solvent.

Examples of $Y^\ominus$ include $C_{1-6}$ alkanoate (such as acetate, or propanoate), with acetate being preferred. $X^\oplus$ includes any pharmaceutically acceptable cation such as protons, alkali metal cations (including but not restricted sodium, and potassium). In a preferred embodiment $X^\oplus$ is a proton.

Ceftaroline fosamil can be provided in a non-hydrated or hydrated form. If it is to be present in the form of a hydrate, it will typically include 1 to 5 mol equivalents of water.

Ceftaroline fosamil can also be provided in the form of a solvate. The type of solvate will depend on the specific application of the medicament. In one embodiment the solvate can be selected from the group consisting of acetic acid, propionic acid and acetonitrile as disclosed in EP-A-1 310 502. Preferably ceftaroline fosamil will be in the form of its acetic acid solvate.

The present invention is illustrated by the following non-limiting examples.

EXAMPLES

Example 1

[4-(4-Pyridyl)-1,3-thiazol-2-yl]thioacetate 1.0 g [4-(4-Pyridyl)-1,3-thiazol-2-yl]thiol were suspended in 5 ml acetic anhydride and 0.69 tetramethylguanidine were added at 0° C. The mixture was stirred for 2.5 h, filtered and washed with 10 ml diethylether and dried in vacuo.

Yield: 0.73 g $^1$H-NMR (CDCl$_3$) δ 2.48 (s, 3H), 7.69 (m, 2H), 7.81 (s, 1H), 8.59 (m, 2H)

$^{13}$C-NMR (CDCl$_3$) δ 30.5, 119.8, 120.5, 140.5, 150.5, 152.7, 155.9, 190.9

Example 2

N-Methyl-4-(2-acetylthio-1,3-thiazol-4-yl)pyridinium iodide 0.73 g [4-(4-Pyridyl)-1,3-thiazol-2-yl]thioacetate were dissolved in 10 ml tetrahydrofuran and 3.0 g methyl iodide were added. The reaction mixture was stirred overnight at ambient temperature, the crystalline precipitate was filtered and washed with 5 ml THF.

Yield: 0.7 g $^1$H-NMR (DMSO-d$_6$) δ 2.22 (s, 3H), 4.35 (s, 3H), 8.56 (d, 2H; J=6.8 Hz), 9.04 (d, 2H; J=6.8 Hz), 9.11 (s, 1H)

$^{13}$C-NMR (DMSO-d$_6$) δ 22.0, 47.4, 123.1, 129.0, 146.1, 146.3, 149.9, 166.5, 167.0

Example 3

N-Methyl-4-(2-acetylthio-1,3-thiazol-4-yl)pyridinium iodide 20.0 g [4-(4-Pyridyl)-1,3-thiazol-2-yl]thiol were suspended in 100 ml acetic anhydride and 13.8 g tetramethylguanidine were added at 0° C. The mixture was stirred for 4 h and then cooled to −20° C. The precipitate was filtered and washed with 20 ml cooled acetic anhydride and dried in vacuo. 21.5 g wet product were dissolved in 200 ml tetrahydrofuran and 80 g methyl iodide were added. The reaction mixture was stirred overnight at ambient temperature, the yellow crystalline precipitate was filtered and washed with 30 ml THF.

Yield: 34.5 g $^1$H-NMR (DMSO-d$_6$) δ 2.22 (s, 3H), 4.35 (s, 3H), 8.56 (d, 2H; J=6.8 Hz), 9.04 (d, 2H; J=6.8 Hz), 9.11 (s, 1H)

$^{13}$C-NMR (DMSO-d$_6$) δ 22.0, 47.4, 123.1, 129.0, 146.1, 146.3, 149.9, 166.5, 167.0

Example 4

[4-(N-Methylpyridinium-4-yl)-1,3-thiazol-2-yl]thiolate 34.5 g N-Methyl-4-(2-acetylthio-1,3-thiazol-4-yl)pyridinium iodide were dissolved in 360 ml MeOH/240 ml water and cooled to 0° C. The pH was adjusted to 7.6 to 8.0 by addition of saturated sodium bicarbonate solution and the mixture was stirred for 4 h. The crystals were filtered and washed with 60 ml water and dried in vacuo.

Yield: 15.0 g $^1$H-NMR (DMSO-d$_6$) δ 4.22 (s, 3H), 8.06 (s, 1H), 8.30 (d, 2H; J=6.7 Hz), 8.78 (d, 2H; J=6.7 Hz)

$^{13}$C-NMR (DMSO-d$_6$) δ 46.7, 122.0, 122.2, 144.9, 147.2, 147.8, 186.3

Example 5

4-Acetyl-1-methylpyridinium iodide

The title compound was prepared according Jun et al., *Letters in Organic Chemistry*, 2009, 6, 500-503.

20.0 g 4-Acetylpyridine were dissolved in 200 ml ethyl acetate and 117.2 g methyl iodide were added. After refluxing for 2 h the precipitate was filtered and washed with ethyl acetate and dried.

Yield: 38.0 g $^1$H-NMR (DMSO-d$_6$) δ 2.75 (s, 3H), 4.43 (s, 3H), 8.48 (d, 2H; J=6.3 Hz), 9.21 (d, 2H; J=6.3 Hz)

$^{13}$C-NMR (DMSO-d$_6$) δ 27.4, 48.2, 125.5, 147.0, 148.0, 195.7

Example 6

4-(2-Bromoacetyl)-1-methylpyridinium bromide 10.0 g 4-Acetyl-1-methylpyridinium iodide were dissolved in 75 ml hydrogen bromide/acetic acid at 0° C. and 8.6 g bromine dissolved in 40 ml hydrogen bromide/acetic acid were added dropwise. The reaction mixture was added to 800 ml diethylether and the precipitate was filtered, washed with diethyl ether and dried in vacuo to give 14.3 g of the desired product.

$^1$H-NMR (DMSO-d$_6$) δ 4.46 (s, 3H), 5.12 (s, 2H), 8.55 (d, 2H; J=6.6 Hz), 9.26 (d, 2H; J=6.6 Hz)

$^{13}$C-NMR (DMSO-d$_6$) δ 34.4, 48.2, 125.7, 145.9, 146.9, 189.0

Example 7

4-Acetyl-1-methylpyridinium methylsulfate 2.0 g 4-Acetylpyridine were dissolved in 10 ml acetonitrile and 2.0 g dimethyl sulfate were added. After refluxing for 5 h, the solution was added dropwise to 40 ml ethyl acetate and the precipitate was filtered, washed with ethyl acetate and dried in vacuo.

Yield: 2.31 g $^1$H-NMR (DMSO-d$_6$) δ 2.75 (s, 3H), 3.38 (s, 3H), 4.43 (s, 3H), 8.47 (d, 2H, J=6.5 Hz), 9.19 (d, 2H, J=6.6 Hz)

$^{13}$C-NMR (DMSO-d$_6$) δ 27.3, 48.2, 52.8, 125.5, 147.0, 148.1, 195.7

Example 8

4-(2-Chloroacetyl)-1-methylpyridinium chloride 15.78 g 4-Acetyl-1-methylpyridinium iodide were suspended in 60 ml acetic acid and 15.0 g sulfuryl chloride were added. The mixture was stirred at ambient temperature for several hours and cooled to 0° C. The crystals were filtered, washed with acetic acid and dried.

Yield: 8.4 g $^1$H-NMR (CD$_3$COOD-d$_6$) δ 4.72 (s, 3H), 5.20 (s, 2H), 8.65 (d, 2H; J=6.0 Hz), 9.29 (d, 2H; J=6.1 Hz)

Example 9

N-Methyl-4-(2-mercapto-1,3-thiazol-4-yl)pyridinium bromide 0.69 g Ammonium dithiocarbamate were dissolved in 10 ml MeOH and 1.47 g 4-(2-bromoacetyl)-1-methylpyridinium bromide were added. After 2 h at ambient temperature the mixture was refluxed. After cooling the precipitate was filtered, washed with MeOH and dried.

Yield: 0.15 g $^1$H-NMR (DMSO-d$_6$) δ 4.32 (s, 3H), 8.32 (s, 1H), 8.45 (d, 2H; J=6.9 Hz), 9.08 (d, 2H; J=6.8 Hz), 14.1 (br s, 1H)

$^{13}$C-NMR (DMSO-d$_6$) δ 47.3, 121.6, 122.5, 136.6, 141.3, 145.9, 190.2

Example 10

[4-(N-Methylpyridinium-4-yl)-1,3-thiazol-2-yl]thiolate 0.69 g Ammonium dithiocarbamate were dissolved in 10 ml EtOH and 1.47 g 4-(2-bromoacetyl)-1-methylpyridinium bromide were added. After 1 h at ambient temperature 10 ml EtOH were added and the mixture was refluxed for 3 h. After cooling 10 ml water were added and the pH was adjusted to 8 by saturated sodium bicarbonate solution. The precipitate was filtered, washed with EtOH and dried.

Yield: 0.16 g $^1$H-NMR ($CD_3COOD$) δ 4.46 (s, 3H), 8.01 (s, 1H), 8.37 (d, 2H; J=6.8 Hz), 8.94 (d, 2H; J=6.8 Hz)

$^{13}$C-NMR ($CD_3COOD$) δ 47.7, 121.2, 123.0, 136.0, 142.0, 146.1, 191.3

Example 11

Benzhydryl 7β-[(phenylacetyl)amino]-3-[4-(1-methyl-4-pyridinio)-2-thiazolythio]-3-cephem-4-carboxylate iodide 1.18 g of benzhydryl 7β-[(phenylacetyl)amino]-3-[(methylsulfonyl)oxy]-3-cephem-4-carboxylate (MW 578.67, 2 mmol, 1 eq.) were dissolved in 20 mL of acetonitrile. To the solution was added 0.76 g of 4-(2-acetylthio-thiazol-4-yl)-1-methyl-pyridinium iodide (MW 378.26, 2 mmol, 1 eq.), 14 mg 4-dimethylaminopyridine (MW 122.17, 0.01 mmol, 0.06 eq.) and 20 mg of sodium hydrogen carbonate (MW 84.01, 2.4 mmol, 1.2 eq.). The reaction mixture was stirred at ambient temperature for 16 hours. Then the mixture was filtered and the cake was washed with 3 mL of acetonitrile. The filtrate was concentrated in vacuo. The residue was dissolved in 6 mL and the resulting solution was added to 80 mL of methyl-tert.-butyl ether. After stirring for 30 min the precipitate was isolated by filtration, washed with 20 mL of methyl-tert.-butyl ether and dried in vacuo.

Yield: 1.46 g $^1$H-NMR (DMSO-d6, 500 Mz) δ (ppm)=3.55 (dd, $CH_2$, 2H, J 13.8 Hz, J 30.1 Hz), 3.73 and 4.01 (ABq, $CH_2$, 2H, J 17.6 Hz), 4.33 (s, $CH_3$, 3H), 5.32 (d, CH, 1H, J 5.0 Hz), 5.90 (dd, CH, 1H, J 5.0 Hz, J 9.6 Hz), 6.99 (s, CH, 1H), 7.19 (m, CH, 15H), 8.53 (d, CH, 1H, J 8.1 Hz), 9.01 (d, CH, 2H, J 8.1 Hz), 9.01 (s, CH, 1H) and 9.30 (d, NH, 1H, J 8.4 Hz).

$^{13}$C-NMR (DMSO-d6, 300 Mz) δ (ppm)=29.52, 41.53, 47.29, 59.72, 79.73, 116.30, 123.10, 126.46, 126.52, 127.00, 127.91, 128.23, 128.27, 128.42, 128.95, 131.69, 135.67, 139.05, 139.27, 146.03, 146.50, 149.54, 160.33, 164.03, 164.76, 170.05.

Example 12

Benzhydryl 7β-[(phenylacetyl)amino]-3-[4-(1-methyl-4-pyridinio)-2-thiazolythio]-3-cephem-4-carboxylate tetrafluoroborate 1.20 g of benzhydryl 7β-[(phenylacetyl)amino]-3-[(methylsulfonyl)oxy]-3-cephem-4-carboxylate (MW 578.67, 2.1 mmol, 1 eq.) were dissolved in 20 mL of acetonitrile. To the solution were added 0.66 g of 4-(2-mercapto-thiazol-4-yl)-1-methyl-pyridinium tetrafluoroborate (MW 296.12, 2.2 mmol, 1.1 eq.) and 0.16 g sodium hydrogen carbonate (MW 84.01, 1.9 mmol, 0.91 eq.). The reaction mixture was stirred at ambient temperature for 17 hours. Then the mixture was filtered and washed with 3 mL of acetonitrile. The filtrate was concentrated in vacuo. The residue was dissolved in 6 mL acetonitrile and the resulting solution was added dropwise to 80 mL of methyl-tert.-butyl ether. After stirring for 30 minutes the precipitate was isolated by filtration, washed with 20 mL of methyl-tert.-butyl ether and dried in vacuo.

Yield 1.45 g $^1$H-NMR (DMSO-d6, 500 Mz) δ (ppm)=3.55 (q, $CH_2$, 2H), 3.77 and 4.01 (ABq, $CH_2$, 2H, J 17.6 Hz), 4.33 (s, $CH_3$, 3H), 5.32 (d, CH, 1H, J 5.0 Hz), 5.90 (dd, CH, 1H, J 5.0 Hz, J 9.6 Hz), 7.00 (s, CH, 1H), 7.19 (m, CH, 15H), 8.53 (d, CH, 1H, J 8.1 Hz), 8.98 (s, CH, 1H, J Hz), 8.99 (d, CH, 2H, J 8.1 Hz) and 9.30 (d, CH, 1H, J 8.1 Hz).

$^{13}$C-NMR (DMSO-d6, 300 Mz) δ (ppm)=29.52, 41.53, 47.26, 59.73, 79.33, 116.29, 123.10, 126.47, 126.51, 127.01, 127.93, 128.23, 128.26, 128.41, 128.95, 131.69, 135.67, 139.05, 139.27, 146.03, 146.51, 149.56, 160.33, 164.05, 164.77, 170.95.

Example 13

Benzhydryl 7β-[(phenylacetyl)amino]-3-[4-(1-methyl-4-pyridinio)-2-thiazolythio]-3-cephem-4-carboxylate trifluoromethane sulfonate 0.60 g of benzhydryl 7β-[(phenylacetyl)amino]-3-[(methylsulfonyl)oxy]-3-cephem-4-carboxylate (MW 578.67, 1 mmol, 1 eq.) were dissolved in 10 ml acetonitrile. To the solution were added 0.40 g of 4-[4-(1-methy)pyridyl]-1,3-thiazole-2-thiole trifluoromethane sulfonate (MW 358.38, 1.1 mmol, 1.1 eq.) and 81 mg of sodium hydrogen carbonate (MW 84.01, 1.9 mmol, 0.96 eq.). The reaction mixture was stirred at ambient temperature for 22.5 hours. Then the mixture was filtered and the cake was washed with 3 mL of acetonitrile. The filtrate was concentrated in vacuo. The residue was dissolved in 2 mL acetonitrile and the resulting solution was added to 40 mL of methyl-tert.-butyl ether. After stirring for 30 min the precipitate was isolated by filtration, washed with 10 mL of methyl-tert.-butyl ether and dried in vacuo.

Yield 0.94 g $^1$H-NMR (DMSO-d6, 500 Mz) δ (ppm)=3.56 (q, $CH_2$, 2H), 3.73 and 3.01 (ABq, $CH_2$, 2H, J 17.6 Hz), 4.33 (s, $CH_3$, 3H), (5.36 (d, CH, 1H, J 5.0 Hz), 5.91 (dd, CH, 1H, J 5.0 Hz, J 9.6 Hz), 6.99 (s, CH, 1H), 7.19 (m, CH, 15H), 8.52 (d, CH, 1H, J 8.1 Hz), 8.99 (s, CH, 1H, J Hz), 8.99 (d, CH, 2H, J 8.1 Hz) and 9.30 (d, CH, 1H, J 8.1 Hz).

$^{13}$C-NMR (DMSO-d6, 300 Mz) δ (ppm)=29.50, 41.53, 47.25, 59.73, 79.33, 116.29, 123.10, 126.47, 126.51, 127.01, 127.93, 128.23, 128.26, 128.41, 128.95, 131.70, 135.67, 139.05, 139.27, 146.02, 146.51, 149.56, 160.33, 164.06, 164.76, 170.95.

Example 14

4-(2-Mercapto-thiazol-4-yl)-1-methyl-pyridinium tetrafluoroborate

To a suspension of 2.09 g of [4-(4-(1-methylpyridyl)-1,3-thiazol-2-yl]thiolate (MW 298.31, 7 mmol, 1 eq.) in 50 mL of acetonitrile was added 2.64 g of aqueous tetrafluoroboric acid 50% (MW 87.81, 15 mmol, 2.1 eq.) acid. To the resulting solution was added 200 mL of methyl-tert.-butyl ether. After stirring for 1 hour at ambient temperature the precipitated yellow crystals were isolated by filtration, washed with methyl-tert.-butyl ether and dried in vacuo.

Yield: 2.81 g (94.6%)

$^1$H-NMR (DMSO-d6, 500 Mz) δ (ppm)=4.29 (s, CH$_3$, 3H), 8.26 (s, CH, 1H), 8.42 (d, CH, 2H, J 6.7 Hz), 9.03 (d, CH, 2H, J 6.7 Hz) and 14.12 (s, 5H, 1H).
$^{13}$C-NMR (DMSO-d6, 500 Mz) δ (ppm)=47.33, 121.43, 122.50, 136.56, 141.32, 145.90.

Example 15

4-(2-Mercapto-thiazol-4-yl)-1-methyl-pyridinium trifluoromethane sulfonate

To a suspension of 8.34 g of [4-(4-(1-methylpyridyl)-1,3-thiazol-2-yl]thiolate (MW 298.31, 28 mmol, 1 eq.) in 200 mL of acetonitrile was added 9.0 g trifluoromethane sulfonic acid (MW 150.08, 30 mmol, 1.1 eq.). To the resulting solution was added 800 mL of methyl-tert.-butyl ether. After stirring for 1 hour at ambient temperature the precipitated crystals were isolated by filtration, washed with methyl-tert.-butyl ether and dried in vacuo.
Yield: 14.44 g (93.7%)
mp: 211° C.
$^1$H-NMR (DMSO-d6, 500 Mz) δ (ppm)=4.30 (s, CH$_3$, 3H), 8.26 (d, CH, 2H, J 6.8 Hz), 9.03 (d, CH, 2H, J 6.8 Hz) and 10.10 (s, 5H, 1H).
$^{13}$C-NMR (DMSO-d6, 500 Mz) δ (ppm)=47.35, 121.43, 122.52, 136.47, 141.34, 145.90.

Example 16

4-(2-Mercapto-thiazol-4-yl)-1-methyl-pyridinium methanesulfonate

To a suspension of 0.42 g of [4-(4-(1-methylpyridyl)-1,3-thiazol-2-yl]thiolate (MW 298.31, 1.4 mmol, 1 eq.) in 10 mL of acetonitrile was added 0.29 g methane sulfonic acid (MW 96.11, 3 mmol, 2.2 eq.). After stirring for 1 hour at ambient temperature the precipitated crystals were isolated by filtration, washed with acetonitrile and dried in vacuo.
Yield: 0.50 g (93.7%)
mp: 212° C.
$^1$H-NMR (DMSO-d6, 500 Mz) δ (ppm)=2.33 (s, CH$_3$, 3H), 4.31 (s, CH$_3$, 3H), 8.44 (d, CH, 2H, J 6.6 Hz), 9.06 (d, CH, 2H, J 6.6 Hz) and 14.11 (s, 5H, 1H).
$^{13}$C-NMR (DMSO-d6, 500 Mz) δ (ppm)=39.78, 47.31, 121.55, 122.51, 136.47, 141.28, 145.90.

Example 17

4-(2-Mercapto-thiazol-4-yl)-1-methyl-pyridinium chloride

To a suspension of 0.84 g of [4-(4-(1-methylpyridyl)-1,3-thiazol-2-yl]thiolate (MW 298.31, 1.4 mmol, 1 eq.) in 20 mL of acetonitrile was added 0.56 g trimethylsilyl chloride (MW 108.44, 5.2 mmol, 3.7 eq.) and 0.5 mL methanol. After stirring for 1 hour at ambient temperature the precipitated yellow crystals were isolated by filtration, washed with methyl-tert.-butyl ether and dried in vacuo.
Yield: 0.94 g (93.7%)
mp: 245° C.
$^1$H-NMR (DMSO-d6, 500 Mz) δ (ppm)=4.32 (s, CH$_3$, 3H), 8.37 (s, CH, 1H), 8.51 (d, CH, 2H, J 6.7 Hz), 9.10 (d, CH, 2H, J 6.8 Hz) and 14.20 (s, 5H, 1H).
$^{13}$C-NMR (DMSO-d6, 500 Mz) δ (ppm)=47.27, 121.62, 122.58, 136.69, 141.37, 145.90.

Example 18

4-(2-Mercapto-thiazol-4-yl)-1-methyl-pyridinium trifluoroacetate

To a suspension of 0.42 g of [4-(4-(1-methylpyridyl)-1,3-thiazol-2-yl]thiolate (MW 298.31, 1.4 mmol, 1 eq.) in 10 mL of acetonitrile was added 0.34 g trifluoroacetic acid (114.02, 3.0 mmol, 2.2 eq.). Then 40 mL of methyl-tert.-butyl ether were added. After stirring for 1 hour at ambient temperature the precipitated yellow crystals were isolated by filtration, washed with methyl-tert.-butyl ether and dried in vacuo.
Yield: 0.42 g (83.2%)
mp: 195° C.
$^1$H-NMR (DMSO-d6, 500 Mz) δ (ppm)=4.30 (s, CH$_3$, 3H), 8.28 (s, CH, 1H), 8.43 (d, CH, 2H, J 6.7 Hz), 9.05 (d, CH, 2H, J 6.7 Hz) and 13.86 (s, 5H, 1H).
$^{13}$C-NMR (DMSO-d6, 500 Mz) δ (ppm)=47.25, 118.38, 121.79, 122.49, 137.65, 141.85, 145.85, 145.89, 157.68, 158.17

Example 19

4-(2-Mercapto-thiazol-4-yl)-1-methyl-pyridinium toluene-4-sulfonate

To a suspension of 0.42 g of [4-(4-(1-methylpyridyl)-1,3-thiazol-2-yl]thiolate (MW 298.31, 1.4 mmol, 1 eq.) in 10 mL of acetonitrile were added 0.47 g p-toluene sulfonic acid (MW 172.20, 2.7 mmol, 1.9 eq.). After stirring for 1 hour at ambient temperature the precipitated yellow crystals were isolated by filtration, washed with acetonitrile and dried in vacuo.
Yield: 0.28 g (53.6%)
mp: 241° C.
$^1$H-NMR (DMSO-d6, 500 Mz) δ (ppm)=2.29 (s, CH$_3$, 3H), 4.30 (s, CH$_3$, 3H), 8.28 (s, CH, 1H), 8.41 (d, CH, 2H, J 6.9 Hz), 9.03 (d, CH, 2H, J 6.9 Hz) and 14.11 (s, 5H, 1H).
$^{13}$C-NMR (DMSO-d6, 500 Mz) δ (ppm)=20.75, 47.32, 121.50, 122.47, 128.02, 136.49, 137.58, 141.23, 145.71, 145.92.

The invention claimed is:
1. A compound selected from the group consisting of

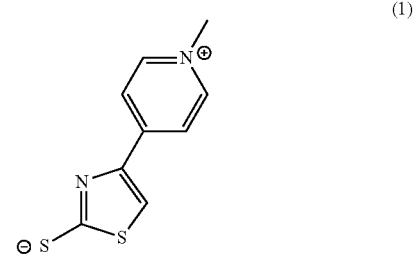

(1)

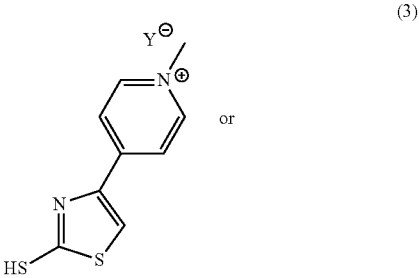

(3)

or (4)

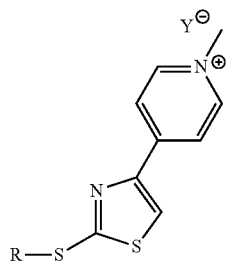

wherein
R is R¹—C(O)— with R¹ being C$_{1-12}$ alkyl or R²—O—C(O)— with R² being C$_{1-4}$ alkyl, benzyl or phenyl; and Y$^\ominus$ is an anion.

2. A compound according to claim 1, wherein Y$^\ominus$ is selected from the group consisting of halogenides, trifluoroacetate, methane sulfonate, trifluoromethane sulfonate, toluene-4-sulfonate, tetrafluoroborate, acetate, hexafluorophosphate and hexafluoroantimonate.

3. A process for producing a compound having a formula (4) comprising the steps of:
   (i) reacting [4-(4-pyridyl)-1,3-thiazol-2-yl]thiol with an acylating agent to provide a compound having the formula (ii)

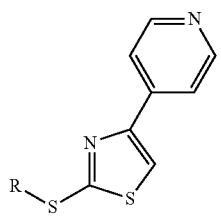 (ii)

wherein R is R¹—C(O)— with R¹ being C$_{1-12}$ alkyl or R²—O—C(O)— with R² being C$_{1-4}$ alkyl, benzyl or phenyl; and
   (ii) reacting the resultant compound having the formula (ii) with a methylating agent to provide the compound having the formula (4)

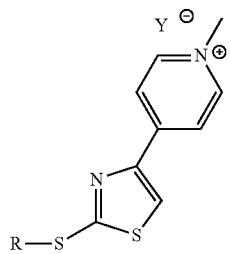

4. A process of preparing a compound having the formula (3) comprising the steps of:
   (i) reacting 4-acetyl-1-methylpyridinium salt to provide 4-(2-halogenoacetyl)-1-methylpydridinium halogenide; and
   (ii) reacting the resultant 4-(2-halogenoacetyl)-1-methylpydridinium halogenide with a dithiocarbamate to provide the compound having the formula (3)

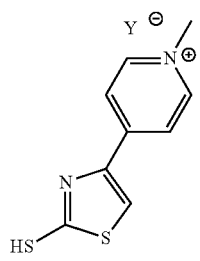 (3)

wherein Y$^\ominus$ is an anion.

5. The process according to claim 4 further comprising the step of:
   (iii) reacting the compound having the formula (3) with an aqueous base to provide a compound having the formula (1)

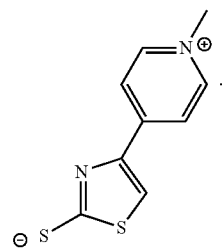 (1)

6. A process for producing a compound having the formula (3) comprising the step of:
   (i) reacting [4-(4-(1-methylpyridyl)-1,3-thiazol-2-yl]thiolate with an acid HY to provide a compound having the formula (3)

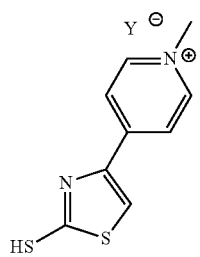 (3)

wherein Y$^\ominus$ is an anion.

7. The process of claim 3 further comprising the step of:
   (iii) reacting the compound having the formula (4) by removing the group R— to provide the compound having the formula (1)

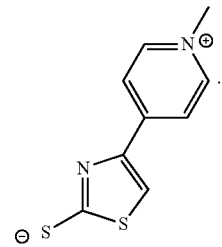 (1)

* * * * *